United States Patent [19]

Korbonits et al.

[11] Patent Number: 4,988,730
[45] Date of Patent: Jan. 29, 1991

[54] DIPHENKYLPROPYLAMINES FOR THE THERAPY OF HEART DISEASE

[75] Inventors: Dezső Korbonits; Pál Kiss, both of Budapest; László Szekeres; Gyula Papp, both of Szeged; Gábor Kovács, Budapest; Andrea Sántáné Csutor, Budapest; Sándor Virág, Budapest; Éva Udvari, Szeged; Imre Bata, Budapest; Katalin Mármarosi née Kellner, Biatorbágy; László Tardos, Budapest; Péter Körmöczy, Budapest; Vera Gergely, Budapest; Zoltán Vargai, Budapest, all of Hungary

[73] Assignee: Chinoin Gyogyszer es Vegyeszeti Termekek Gyar RT, Budapest, Hungary

[21] Appl. No.: 385,539

[22] Filed: Jul. 21, 1989

Related U.S. Application Data

[63] Continuation of Ser. No. 72,457, Jul. 13, 1987, abandoned.

[30] Foreign Application Priority Data

Jul. 11, 1986 [HU] Hungary ............................... 2873/86
May 20, 1987 [HU] Hungary ............................... 2873/86

[51] Int. Cl.⁵ .................. A61K 31/135; A61K 31/36; C07C 87/28; C07D 317/58
[52] U.S. Cl. ..................................... 514/466; 514/563; 514/564; 514/567; 514/616; 514/630; 514/648; 549/437; 549/439; 549/440; 549/443; 562/435; 562/441; 564/157; 564/219; 564/316
[58] Field of Search ............... 564/316, 320, 157, 219; 549/437, 439, 440, 443; 562/435, 441; 514/466, 563, 567, 564, 616, 630, 648

[56] References Cited

FOREIGN PATENT DOCUMENTS 122967 11/1976 German Democratic Rep. .

OTHER PUBLICATIONS

Harsanyi et al., J. Med. Chem., 7,623 (1964).
Benthe et al., C. A., 99:151,647m (1983).
Rajsner et al., C.A., 102, 220,550u (1985) (Abstract of Czech. CS 217,009).
Hackh's Chemical Dictionary, 4th Edition, p. 508, Grant, (1968).

*Primary Examiner*—Nicky Chan
*Attorney, Agent, or Firm*—Herbert Dubno; Jonathan Myers

[57] ABSTRACT

The invention relates to novel diphenylpropylamine derivatives of the general formula (I).

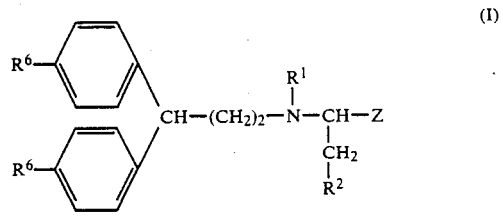

$R^1$ stands for hydrogen or a methyl group;
$R^2$ stands for hydrogen, a methyl or n-decyl group;
Z means a phenyl group substituted by $R^3$, $R^4$ and $R^5$, wherein
  $R^3$ means hydrogen, fluorine, chlorine or bromine, or a nitro, $C_{1-12}$alkyl, $C_{1-4}$alkoxy, phenoxy or benzyloxy group;
  $R^4$ and $R^5$ represent hydrogen, chlorine or a hydroxy, alkoxy, benzyloxy, acetamino or carboxy group; or
  $R^4$ and $R^5$ together form a methylendioxy group;
or
Z may stand for a 4-methoxynaphtyl or 4-ethoxynaphthyl group; and
$R^6$ stands for hydrogen or fluorine, with the proviso that each of $R^1$, $R^2$, $R^3$, $R^4$ and $R^6$ cannot simultaneously stand for hydrogen, as well as their physiologically acceptable acid addition salts.

The invention also relates to a process for the preparation of these compounds and to the pharmaceutical compositions containing these compounds.

The compounds of the general formula (I) can preferably be used for the treatment of cardiovascular diseases.

6 Claims, No Drawings

DIPHENKYLPROPYLAMINES FOR THE THERAPY OF HEART DISEASE

This is a continuation of co-pending application Ser. No. 07/072,457 filed on 13 Jul. 1987, now abandoned.

The invention realtes to novel diphenylpropylamine derivatives, to their therapeutically preferable salts as well as to a process for the preparation of these compounds which can mainly be used for the treatment of cardiovascular diseases.

It is known that several diphenylpropylamine derivatives possess advantageous properties for the therapy of heart diseases such is e.g. prenylamine [Arzneimittelforschung 10, 569, 573 and 583 (1960); Arch. Pharm. 295,196 (1962)]. Also fendiline [N-(3,3-diphenylpropyl)-α-methylbenzylamine], a calcium antagonist with a coronary dilating action, is widely used for the treatment of ischaemic heart diseases such as angina pectoris and of some other cardiovascular diseases (HU-PS 150,534). A number of fendiline derivatives have been prepared, wherein one or both phenyl groups of the diphenylpropylamino moiety bear one or more substituents; however, according to the publications, none of these derivatives showed a biologic action surpassing that of fendiline [J. für Prakt. Chem. 34, (1966); Magy. Kém. Folyóirat 74, 20 (1968)].

Surprisingly, it has now been found that the novel compounds of the formula (I) as well as their salts,

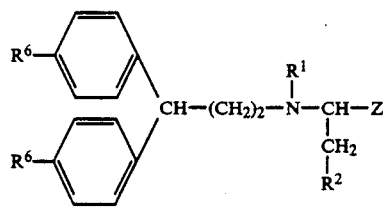

wherein
$R^1$ stands for hydrogen or a methyl group;
$R^2$ stands for hydrogen, a methyl or n-decyl group;
Z means a phenyl group substituted by $R^3$, $R^4$ and $R^5$, wherein

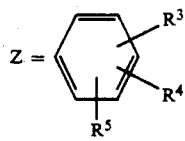

$R^3$ means hydrogen, fluorine, chlorine or bromine, or a nitro, $C_{1-12}$alkyl, $C_{1-4}$alkoxy, phenoxy or benzyloxy group;

$R^4$ and $R^5$ represent hydrogen, chlorine or a hydroxy, alkoxy, benzyloxy, acetamino or carboxy group; or $R^4$ and $R^5$ together form a methylendioxy group; or Z may stand for a 4-methoxynaphthyl or 4-ethoxynaphthyl group; and $R^6$ stands for hydrogen or fluorine, with the proviso that $R^1$, $R^2$, $R^3$, $R^4$, $R^5$ and $R^6$ cannot all simultaneously stand for hydrogen, possess preferable biologic effects.

Thus, such derivatives forming a more preferred group of the compounds of the formula (I), wherein $R^1$ is as defined above, $R^2$ means a methyl group, $R^3$ is halogen and $R^4$, $R^5$ and $R^6$ stand for hydrogen, show significant antianginal effects. In these derivatives, the halogen may be fluorine, chlorine or bromine. Thus, 2-(4-chlorophenyl)-6,6-diphenyl-3-azahexane hydrochloride shows an extraordinarily strong effect in rats on the acute coronary failure induced by vasopressin. The $ED_{50}$ value of this compound is 0.054 mg/kg when it is intravenously (i.v.) administered at 2 minutes before inducing the angina by the intravenous administration of 2 NE/kg of vasopressin. For comparison, the $ED_{50}$ value of fendiline determined under the same conditions is 2.30 mg/kg. Thus, the above compound of the invention is about 42 times as effective as fendiline under the same conditions.

Another, more preferred group of the compounds of formula (I) which are endowed of highly preferred therapeutic effects, are derivatives, wherein both $R^1$ and $R^2$ are hydrogen and the benzene ring of the phenylethyl moiety is polysubstituted. In this case a very preferable meaning of $R^3$ is an alkoxy group. The compounds of this type show not only an antianginal action which is characteristic of fendiline, however, that of the compounds of the formula (I) is stronger and more protracted, but, suprisingly, they also possess other effects of new type which are advantageous in the heart therapy. Thus, the strength and duration of the effect of 2-(3,4-dimethoxyphenyl)-6,6-diphenyl-3-azahexane (the hydrochloride of this substance is designated) as KHL-8430, hereinafter) in rats on the angina induced by vasopressin or in dogs on the ischaemic state induced by coronary occlusion highly exceed that of fendiline and in addition, this substance is less toxic than the reference compound on both intravenous and oral administrations.

In the case of the vasopressin angina of rats [Papp and Szekeres: Arch. int. Pharmacodyn. 160, 147 (1966)], the antianginal activity measured at the 2nd minute following the intravenous administration or at the 60th minute after oral administration, respectively, as well as the intravenous and oral acute toxicity values, the therapeutic indices and the quotient of the therapeutic ratio of KHL-8430 to that of fendiline as measured in rats are summarized in Table 1.

TABLE 1

| | Intravenous administration | | | | Oral administration | | | |
|---|---|---|---|---|---|---|---|---|
| Compound | $ED_{50}$ mg/kg | $LD_{50}$ mg/kg | $\dfrac{LD_{50}}{ED_{50}}$ | Quotient* of the therapeutic ratios | $ED_{50}$ mg/kg | $LD_{50}$ mg/kg | $\dfrac{LD_{50}}{ED_{50}}$ | Quotient* of the therapeutic ratios |
| KHL-8430 | 0.34 | 16.0 | 47.1 | 8.89 | 8.4 | 1400 | 166.7 | 4.17 |
| Fendiline | 2.30 | 12.2 | 5.3 | | 20.0 | 800 | 40.0 | |

*Quotient = $\dfrac{\text{KHL-8430 therapeutic ratio}}{\text{Fendiline therapeutic ratio}}$ The myocardial ischaemia induced by coronary occlusion in dogs [Szekeres et al.: J. Pharm. Exp. Ther. 196, 15 (1976)] is decreased more strongly and with a much longer duration by KHL-8430 than by fendiline either on intravenous or oral administration.

According to a more detiled haemodynamic study carried out on dogs, in comparison with fendiline and some other known calcium antagonists (such as verapamil or nifedipine), the arterial blood pressure during coronary occlusion is only a little lowered, the heart rate is not decreased and the prolongtion of the activation time in the ischaemic area is significantly restrained by KHL-8430 which latter is an important factor in the development of the so-called "re-entry" type arrhythmias.

Thus, as opposed to fendiline, KHL-8430 is surprisingly capable to restrain the ventricular extrasystoles developing under the effect of a coronary occlusion and has in situ both in the auricular and ventricular muscle of the isolated cat heart a high antiarrhythmic action, which equals the effect of mexiletine, and antiarrhythmic drug widely used in the therapy, and by far surpassing that of fendiline, verapamil and other calcium antagonists. In conscious dogs, the extrasystolic activity following by 24 hours the "two-step" coronary occlusion of Harris is significantly lowered by a 2 mg/kg intravenous dose of KHL-8430, whereas no significant effect is exerted by either fendiline or verapamil in this arrhytimia model. Similarly, the frequency of the extrasystoles is diminished in a dose-dependent manner and very significantly after the oral administration of KHL-8430. The high activity of KHL-8430 is indicated by the fact that in a great part of the cases, the rhythm disturbances of the heart could be suspended.

A specific advantage also is that the strong anti-ischaemic protective action after an oral dose of KHL-8430 is very smooth, whereby the adjustment of a steady blood level, which is very desirable for the therapy, is promoted to a great extent.

According to an in-depth study on the mechanism, these very favorable therapeutic effects of the heart are due above all to the organ-specific calcium antagonist properties mainly appearing in the coronary vessels as well as to the fast sodium channel-inhibition. Again, as opposed to fendiline and other calcium antagonists, the substances belonging to this more restricted group of the compounds of formula (I) do not show any cardiodepressant action in the antianginal-antiarrhythmic dose interval, a fact providing an outstanding advantage.

By comprising the haemodynamically active (hypotensive and left ventricle contractility-decreasing) as well as anti-ischaemic ("antianginal") and antiarrhythmic ("antifibrillatory") $ED_{25}$ values of the intravenous administered KHL-8430, verapamil and fendiline, it appeared that the "haemodynamical therapeutic index" of KHL-8430 is by far the best among the three calcium antagonists studied.

| Anti-Ischemic, Antiarrythmic and Haemodynamic Actions of Calcium Antagonists Compared By $ED_{50}$ Values In Mg/Kg | | | |
|---|---|---|---|
| Parameters and the tendency of change | verapamil | fendiline | KHL-8430 |
| Haemodynamical values: | | | |
| BP ↓ | 0.20 | 0.74 | 2.25 |
| HR ↓ | 0.75 | 5.00 | 7.20 |
| DP/dt max ↓ | 0.07 | 0.49 | 6.00 |
| Atrial FFT ↑ | 1.5 | 2.8 | 1.8 |
| Vasopressin-induced angina BP/Antianginal $ED_{50}$ | 0.1 | 1.2 | 0.6 |
| | 2.0 | 0.62 | 3.75 |
| $\frac{BP}{Atrial\ FFT}$ $ED_{25}$ | 0.13 | 0.26 | 1.25 |
| $\frac{D/dt\ max}{antianginal}$ $ED_{25}$ | 0.7 | 0.41 | 10.00 |
| $\frac{dP/dt\ max}{Atrial\ FFT}$ $ED_{25}$ | 0.04 | 0.175 | 3.33 |

Notes:
BP: blood pressure; HR: heart rate; DP/dt max: contractility (contractile force) of the left ventricle; FFT: fibrillation threshold.

According to an other aspect of the invention, there is provided a process for the preparation of the new compounds of the formula (I) and salts thereof which comprises: in order to obtain preferred compounds of the formula (I), wherein $R^1$ stands for hydrogen, (a) subjecting to reductive condensation reaction a diphenylpropylamine derivative of the formula (II),

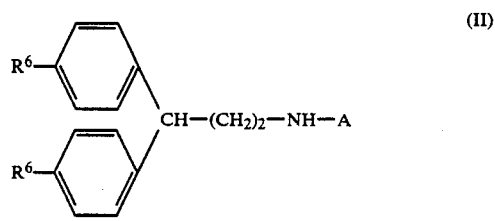

(II)

wherein A stands for hydrogen and $R^6$ is as defined above with a ketone of the formula (III),

(III)

wherein $R^2$ and Z are as defined above, in a single step or, if desired, in tewo steps; or (b) reacting a compound of the formula (IV),

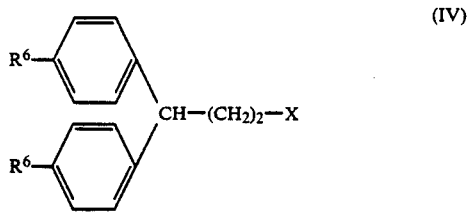

(IV)

wherein X means halogen, preferably chlorine, bromine or iodine, and R⁶ is as defined above, with an amine of the formula (V),

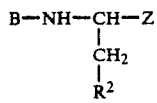  (V)

wherein B stands for hydrogen or a benzyl group, and R² as well as Z are as defined above, and debenzylating a thus-obtained compound, wherein B means a benzyl group; or (c) reacting an amine of the formula (II) wherein A represents hydrogen or a benzyl group and R⁶ is as defined above, with a compound of the formula (VI),

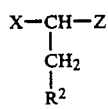  (VI)

wherein R², Z and X are as defined above and debenzylating a thus-obtained compound wherein A means a benzyl group; or (d) subjecting to reductive condensation reaction a diphenylpropionaldehyde of the formula (VII),

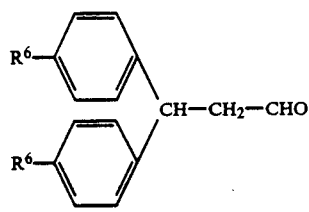  (VII)

wherein R⁶ is as defined above, with an amine of the formula (V), wherein B stands for hydrogen and R² and Z are as defined above, in a single step or in two steps; or (e) reacting a diphenylacetonitrile of the formula (VIII),

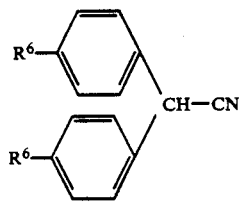  (VIII)

wherein R⁶ is as defined above, with a compound of the formula (IX),

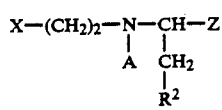  (IX)

wherein R², Z and X are as defined above and A means a benzyl group and substituting in the thus-obtained compound both the cyano and benzyl group for hydrogen; or (f) reacting an amine of the formula (X),

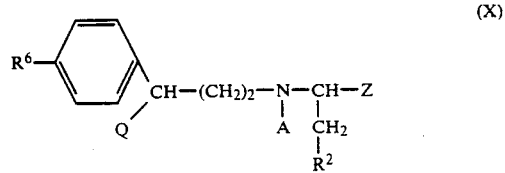  (X)

wherein Q stands for halogen or a hydroxy group, A means hydrogen or a benzyl group, and R², R⁶ as well as Z are as defined above, or a salt thereof with benzene or fluorobenzene in a Friedel-Crafts reaction and debenzylating a thus-obtained compound, wherein A means a benzyl group and, if desired, converting the thus-obtained compound of the formula (I) to a therapeutically well acceptable salt with an inorganic or organic acid.

A specific group of the compounds of formula (I), wherein R¹ stands for a methyl group can preferably be prepared (g) by transforming a compound of the formula (I), wherein R¹ is hydrogen, R², R⁶ and Z and as defined above, to a tertiary amine by methylating on the nitrogen by using a method known per se; or (h) by reacting an amine of the formula (XI),

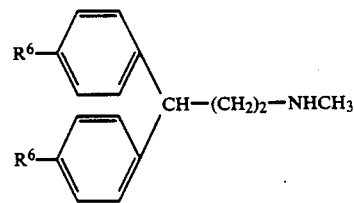  (XI)

wherein R⁶ is as defined above, with a compound of the formula (VI), wherein R², X and Z are as defined above; or (i) reacting an amine of the formula (XII)

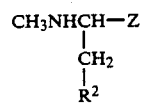  (XII)

wherein Z and R² are as defined above, with a compound of the formula (IV), wherein R⁶ and X are as defined above and if desired, converting the thus-obtained compound of the formula (I) to a therapeutically well acceptable salt with an inorganic or organic acid.

In the processes (a) and (d) of the invention, the reductive condensation may be carried out in two steps in such a way that the primary amine of the formula (II) is reacted with the carbonyl compound of the formula (III) or, the amine of the formula (V) is reacted with the carbonyl compound of the formula (VII), respectively, to give a Schiff's base of the formula (XIII)

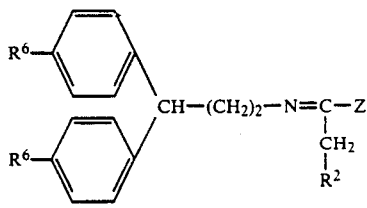

(XIII)

or (XIV)

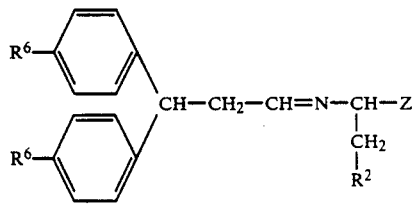

(XIV)

which are then reduced to the compounds of the formula (I). This condensation may be accomplished in an organic solvent, e.g. benzene, toluene or xylene. For promoting the reaction, a Dean-Stark water-separating device may be used. However, the condensation may also be performed by mixing the amine with the carbonyl component while promoting the water elimination by heating and working under reduced pressure.

The Schiff's base is preferably reduced by catalytic hydrogenation, by using the common metal and noble metal catalysts such as nickel, palladium and platinum. These catalytic reductions may be carried out under atmospheric pressure or at a hydrogen overpressure, at a temperature of 20° to 120° C., preferably at 18° to 30° C. under a pressure of 10,000–100,000 Pa. Suitable solvents are alcohols (e.g. methanol or ethanol) or dioxane. The reduction may also be accomplished by using chemical reducing agents, e.g. complex metal hydrides, preferably sodium borohydride or aluminum amalgam or sodium amalgam or by using an electrolytic reduction method.

The reductive condensation may be accomplished also in a single step by using ethanol as solvent and palladium or charcoal as reducing agent.

In the processes (b), (c), (h) and (i), ethyl ether, dichloromethane, chloroform, benzene, acetone or alcohols and most preferably dimethylformamide may be used as solvents. The coupling may be accelerated by heating to a temperature of 50° to 150° C. The hydrogen halide formed in the reaction may be bound by the common inorganic bases, preferably by potassium carbonate, however, the reaction may also be carried out in the presence of teritary organic bases or of an excess of the reacting amine.

In the process (e) of the invention, the reaction may be performed in the presence of the usual acid binding agents. In the first step, a cyano-substituted compound of the formula (I) is formed in which the cyano group may be replaced by hydrogen in a known way. This process may preferably be carried out in such a way that sodium amide is used both as acid binding agent and cyano group-removing agent in the presence of an inert solvent such as toluene or benzene.

In the process (f), the methods described in the DD-PS No. 33,285 may be used. The reaction is accomplished by using a Friedel-Crafts catalyst, preferably aluminium chloride in benzene at the boiling point of the mixture, whereby benzene is also reactant. However, as starting compound an 1-phenyl-1,2-alkenylamine may also be used which may preferably be prepared from the appropriate compound of the formula (X) by dehydration or by elimination of hydrogen halide.

The starting materials of the formula (X) may be prepared in such a way that 3-hydroxy-3-phenyl-propylamine is subjected to a reductive condensation with an appropriate ketone of the formula (III) and, if desired, the hydroxy group is replaced by chlorine by using thionyl chloride. However, the hydroxy group may also be replaced on the effect of the hydrogen halide formed in the Friedel-Crafts reaction.

The protective groups A and B can be removed in a nearly quantitative yield with catalytic hydrogenation by using platinum oxide or palladium catalyst in acetic acid as solvent.

The process (g) may preferably be accomplished by transforming the compounds of the formula (I), wherein $R^1$ stands for hydrogen to tertiary amines, wherein $R^1$ means a methyl group by heating with an aqueous formaldehyde solution in formic acid.

The processes (h) and (i) may preferably be carried out similarly to processes (b) and (c).

The compounds of the formula (I) can be converted to their salts by using organic or inorganic acids. Hydrochloric, sulfuric, phosphoric, lactic, tartaric, citric, maleic and nicotinic acids may preferably be used as inorganic or organic salt forming agents.

The compounds of the formula (I) and their salts can be formulated to pharmaceutical compositions by mixing them with indifferent non-toxic, inorganic and/or organic carriers as well as with other auxiliary materials commonly used in the pharmaceutical industry. Such compositions are the tablets, film-coated tablets, dragées, enteric-coated dragées, suppositories, capsules, microcapsules, solid or liquid suspensions, emulsions and solutions. Talc, various dextrin derivatives, gelatine, water and polyalkylene alcohols may preferably be employed as carriers. The compositions may also contain other additives such as emulsifying and suspending agents, salts, buffers, disintegrating agents as well as other therapeutically active ingredients.

The compounds of the invention may be used in doses of 1 to 300 mg as depending from the route of the administration, therapeutic purpose, body-weight and age of the patient and other conditions.

The invention is illustrated in detail by the aid of the following non-limiting Examples.

EXAMPLE 1

(a)

N-(α-Methyl-3,4-dimethoxy-benzylidene)-3,3-diphenyl-propylamine [compound of the formula (XIII), $R^2$=H, Z=3,4-dimethoxyphenyl]

The mixture of 84.5 g (0.4 mole) of 3,3-diphenyl-propylamine and 72.1 g (0.,4 mole) of 3,4-dimethoxyacetophenone is heated at 90° C., under a pressure of 130 to 160 Pa for 10 hours under stirring whilst the water formed is continuously distilled off. After cooling, the crude, solidified title compound is obtained in a quantitative yield of 149.5 g (the oretical yield), m.p.: 97°–102° C. After recrystallization from ethanol, the melting point raises to 105°–106° C.

(b) 2-(3,4-Dimethoxyphenyl)-6,6-diphenyl-3-azahexane hydrochloride [compound of the formula (I), $R^1=R^2=H$, Z=3,4-dimethoxyphenyl; compound KHL-8430 (code number)]

To a suspension of the crude Schiff's base prepared as described in Example 1(a) in 1000 ml of methanol, 37.8 g (1.0 mole) of sodium borohydride are portionwise added during 40 minutes, then the mixture is stirred for 3 hours. The solvent is evaporated in vacuo, 800 ml of water are added to the residue which is then extracted 3 times with 200 ml of chloroform each. The organic phases are combined and evaporated. After acidifying with hydrogen chloride in ethyl acetate to pH 1, 145.0 g (88%) of the title compound are obtained, m.p.: 171°–173° C. (after recrystallization from aqueous ethanol).

(c) 2-(3,4-Dimethoxyphenyl)-6,6-diphenyl-3-azahexane hydrochloride

A mixture containing 112.04 g (0.3 mole) of the recrystallized Schiff's base (prepared as described in Example 1(a)) and 16 g of 10% palladium-on-charcoal in 500 ml of ethanol is hydrogenated at 25° C. under atmospheric pressure until the hydrogen uptake ceases. After filtration and evaporation, the residue is acidified with 30 ml of 37% hydrochloric acid and the salt formed is mixed with 140 ml of water to give 119 g (96.3%) of the title compound, m.p.: 171°–173° C.

(d) 2-(3,4-Dimethoxyphenyl)-6,6-diphenyl-3-azahexane hydrochloride

A mixture containing 21.1 g (0.1 mole) of 3,3-diphenylpropylamine and 18.0 g (0.1 mole) of 3,4-dimethoxyacetophenone in 200 ml of xylene is boiled in an apparatus fitted with a Dean-Stark device until the separation of water ceases. The solvent is evaporated in vacuo and the residue, i.e. 75 g of the Schiff's base is hydrogenated in 250 ml of ethanol containing 2 g of 10% palladium-on-charcoal as described in Example 1(c) to give 31.5 g (84%) of the title compound.

(e) 2-(3,4-Dimethoxyphenyl)-6,6-diphenyl-3-azahexane hydrochloride

A mixture containing 21.1 g (0.1 mole) of 3,3-diphenylpropylamine, 18.0 g (0.1 mole) of 3,4-dimethoxyacetophenone and 2 g of 10% palladium-on-charcoal is hydrogenated under a pressure of 1.0 MPa. After filtration, evaporation and salt formation with hydrogen chloride in ethyl acetate, the crude product is recrystallized from ethanol to give 27.2 g (73%) of the title compound, m.p.: 171°–173° C.

(f) 2-(3,4-Dimethoxyphenyl)-6,6-diphenyl-3-azahexane sulfate

This salt is obtained from 2-(3,4-dimethoxyphenyl)-6,6-diphenyl-3-azahexane base prepared as described in Example 1(b) with 0.5 molar equivalent of 2N sulfuric acid, m.p.: 195°–198° C.

(g) The hydrobromide melts at 176°–178° C.

(h) The nitrate melts at 150°–152° C.

(i) The nicotinate melts at 105°–106° C.

(j) 2-(3,4-Dimethoxyphenyl)-6,6-diphenyl-3-azahexane hydrochloride

A mixture containing the crude Schiff's base prepared as described in Example 1(a) and 4 g of Raney-nickel in 1000 ml of ethanol is hydrogenated at 20° C., under atmospheric pressure. After filtration and evaporation, the hydrochloride is formed with hydrogen chloride in ethyl acetate or in ethanol to give 145.0 g (88%) of the title compound, m.p.: 171°–173° C.

EXAMPLE 2

(a) 2-(3,4-Dimethoxyphenyl)-6,6-diphenyl-3-azahexane hydrochloride

A mixture containing 28.0 g of 1-bromo-3,3-diphenylpropane, 27.1 g of 1-benzylamino-1-(3,4-dimethoxyphenyl)-ethane and 15.0 g of potassium carbonate in 100 ml of dimethylformamide is heated at 70° C. while stirring for 16 hours. After filtration, the solvent is evaporated in vacuo and the residue dissolved in 100 ml of glacial acetic acid is hydrogenated in the presence of 0.5 g of platinum oxide at 70° C., under a pressure of 0.4 MPa. After ceasing of the hydrogen uptake (about 5 hours), 100 ml of methanol are added, filtered and the solvent is distilled off. The residue is converted to the hydrochloride as described in Example 1(b) and recrystallized from ethanol to give 31.0 g of the title compound, m.p.: 171°–173° C., which is identical with the compound prepared according to Example 1(b).

(b) 3-(3,4-Dimethoxyphenyl)-1-phenyl-2-azabutane

A mixture containing 18.1 g of 1-amino-1-(3,4-dimethoxyphenyl)-ethane (J. Chem. Soc. 1963, 4289), 10,6 g of benzaldehyde and 1 drop of pyridine in 100 ml of methanol is let stand at 20° C. for 2 days, then 3.8 g of sodium borohydride are added during 30 minutes and stirred for additional 3 hours. After evaporation of the solvent, the residue is diluted with water, extracted with chloroform, the organic phase is dried and evaporated to give 27.1 g of the crude title compound, which can directly be used in the process described in Example 6.

EXAMPLE 3

2-(3,4-Dimethoxyphenyl)-6,6-diphenyl-3-azahexane hydrochloride

To a mixture containing 18.1 g of 1-amino-1-(3,4-dimethoxyphenyl)-ethane and 15 g of potassium carbonate in 100 ml of butanol, 23.7 g of 1-chloro-3,3-diphenylpropane dissolved in 50 ml of butanol are dropped during 1 hour under boiling and stirring, then the mixture is boiled until gas evolution ceases. After cooling and evaporation, the hydrochloride salt is formed as described in Example 1(b) and recrystallized twice from aqueous ethanol to give 28.5 g of the title compound, m.p.: 171°–172° C.

EXAMPLE 4

2-(3,4-Dimethoxyphenyl)-6,6-diphenyl-3-azahexane hydrochloride

A mixture containing 21.0 g of 1-amino-3,3-diphenylpropane, 24,5 g 1-bromo-1-(3,4-dimethoxyphenyl)ethane (Bull. Soc. Chim. France, 1973, 2665) and 15 g of potassium carbonate in 80 ml of dimethylformamide is stirred at 50° C. for 15 hours, then filtered and the solvent is evaporated in vacuo. The residue is taken up in chloroform and converted to the hydrochloride according to Example 1(b) which is recrystallized twice from aqueous ethanol to give 24.0 g of the title compound, m.p.: 171°–173° C.

EXAMPLE 5

2-(3,4-Dimethoxyphenyl)-6,6-diphenyl-3-azahexane hydrochloride

A solution of 21.0 g of 3,3-diphenylpropionaldehyde [J. Med. Chem. 7, 623 (1964)] and 18.1 g of 1-amino-1-(3,4-dimethoxyphenyl)-ethane in 180 ml of ethanol is boiled for 40 minutes, then, after adding 2 ml of water, is reacted with 4 g of sodium borohydride at 30°–35° C. for 30 minutes. After evaporation of the ethanol, the residue is treated with water, extracted with chloroform and the chloroform solution is worked up as described in Example 1(b) to give 30.0 g of the title compound, m.p.: 171°–173° C. (after recrystallization from aqueous ethanol).

EXAMPLE 6

2-(3,4-Dimethoxyphenyl)-6,6-diphenyl-3-azahexane hydrochloride 7.1 g of 2-chloroethanol are dropped at 70° C. to a mixture containing 27.1 g of 3-(3,4-dimethoxyphenyl)-1-phenyl-2-azabutane (prepared according to Example 2(b)) and 15.0 g of potassium carbonate in 80 ml of dimethylformamide during 1 hour under stirring, then the stirring is continued for another 5 hours. After filtration and evaporation of the filtrate, the residue is dissolved in 150 ml of chloroform and boiled with 20 ml of thionyl chloride until ceasing of the gas evolution (about 1 hour). After evaporation, the remaining salt is dissolved in water, alkalized under cooling by ice and extracted with ether. The ethereal solution is dried over anhydrous sodium sulfte, filtered and the ether is evaporated to give oily 1-{N-benzyl-N-[1-(3,4-dimethoxyphenyl)-1-ethyl]}-amino-2-chloroethane.

The solution of 16.5 g of the thus-obtained crude oily product in 100 ml of benzene is boiled with 9.7 g of diphenylacetonitrile and 2.5 g of sodium amide for 2 hours under stirring. After cooling, water is added, the benzene layer is separated, filtered and evaporated. The residue is converted with ethanolic hydrogen chloride solution to 1-cyano-1,1-diphenyl-3-{N-benzyl-N-[1-(3,4-dimethoxyphenyl)-1-ethyl]}-aminopropane hydrochloride and recrystallized from ethanol. A solution of 10 g of the thus-obtained hydrochloride in 100 ml of water is made alkaline under cooling and extracted with 100 ml of benzene.

After drying over anhydrous sodium sulfate and filtration, the solution is boiled with 10.0 g of sodium amide for 2 hours under stirring, cooled, filtered and evaporated. The residue is dissolved in 50 ml of concentrated acetic acid and hydrogenated in the presence of 0.1 g of platinum oxide at 70° C., under a pressure of 0.4 MPa (about 5 hours). After adding 50 ml of methanol, the mixture is filtered and evaporated. The hydrochloride is formed with ethanolic hydrogen chloride solution under a mild heating. After recrystallization from aqueous ethanol, 6.2 g of the title compound are obtained, m.p. 171°–172° C.

EXAMPLE 7

2-(3,4-Dimethoxyphenyl)-6,6-diphenyl-3-azahexane hydrochloride 15.1 g of 3-amino-1-hydroxy-1-phenylpropane is stirred with 19.0 g of 3,4-dimethoxyacetophenone at 80° C. under a pressure of 130 to 160 Pa for 16 hours, then cooled and the mixture of 50 ml of methanol and 2 ml of water is added. The mixture is reacted with 3.5 g of sodium borohydride at 30° to 40° C. for 2 hours. After evaporation of the solvent, the residue is taken up in 100 ml of ether and converted to the hydrochloride by adding ethanolic hydrogen chloride solution. To the suspension of the thus-obtained crude 1-hydroxy-1-phenyl-3{N-[1-(3,4-dimethoxyphenyl)-1-ethyl]}aminopropane hydrochloride in 100 ml of benzene, 40 ml of thionyl chloride are added over 40 minutes while stirring and the suspension is stirred at 40° C. for 1 additional hour. The mixture is evaporated by using an under reduced pressure at most at 40° C., the residue is taken up in 100 ml of benzene and reacted with 20 g of aluminium chloride at 55° to 60° C. for 1 hour then under boiling for an additional 2 hours. After cooling the mixture is poured onto crushed ice containing hydrochloric acid. The benzene layer is separated and washed with water. The combined aqueous phase is made strongly alkaline under cooling by ice, extracted with ether and the ethereal phase is dried over sodium sulfate. The title compound is obtained by using ethanolic hydrogen chloride solution, m.p.: 172°–173° C.

EXAMPLE 8

3-Methyl-2,6,6-triphenyl-3-azahexane hydrochloride 5.9 g of 98–100% formic acid are added to 15.8 of 2,6,6-triphenyl-3-azahexane (fendiline) base under cooling then 5.7 g of 30% aqueous formaldehyde solution are added to the thus-formed thick oil during 5 minutes. The mixture is kept at 40° C. until starting of the gas evolution, then the heating is interrupted for 30 minutes. Thereafter, the mixture is stirred at 80° C. for 12 hours and evaporated. The residue is rubbed with 100 ml of 5% hydrochloric acid solution, heated in a steam bath for 10 minutes, then cooled and made alkaline. The base is extracted into chloroform, dried, filtered and evaporated. After dissolving the residue in ether and adding ethereal hydrogen chloride solution, 14.2 g of the title compound are obtained. m.p.: 96° C.

EXAMPLE 9

2-(3,4-Dimethoxyphenyl)-6,6-diphenyl-3-azahexane hydrochloride

A mixture containing 24.5 g of 1-bromo-1-(3,4-dimethoxyphenyl)ethane (Bull. Soc. Chim. France 1973, 2665), 30.0 g of 1,5,5-triphenyl-3-azapentane and 15.0 g of potassium carbonate in 100 ml of dimethylformamide is stirred at 70° C. for 16 hours. After filtration and evaporation of the solvent, the residue is hydrogenated in 100 ml of acetic acid in the presence of 0.5 g of platinum oxide at 70° C. under a pressure of 0.4 Pa, then 100 ml of methanol are added, filtered and the solvent is evaporated. The residue is converted to the hydrochloride as described in Example 1(b) to give 30.0 g of the title compound, m.p.: 171°–173° C. (from aqueous ethanol).

EXAMPLE 10

2-(3,4-Dimethoxyphenyl)-6,6-diphenyl-3-azahexane hydrochloride

A solution containing 24.5 g of 1-bromo-1-(3,4-dimethoxyphenyl)-ethane in 30 ml of butanol is dropped to the mixture of 21.0 g of 3-amino-1,1-diphenylpropane and 10.5 g of sodium hydrogen carbonate over 2 hours while boiling and stirring. The mixture is boiled until the ceasing of the gas evolution, then cooled, filtered and the solvent is evaporated. The residue is converted to the hydrochloride in ethanol with ethereal hydrogen chloride solution. The salt is recrystallized 3 times from aqueous ethanol to give 18.0 g of the title compound, m.p.: 171°–173° C.

EXAMPLES 11 TO 53

The compounds of the formula (I) listed in Table II wherein $R^1$ means hydrogen, can be prepared in similar yields by using the process described in Examples 1(a) and (b). In Table II, the meaning of $R^2$ and Z, the salt-forming acid, melting point as well as the literature reference of the appropriate ketone component are given, when the ketone has been prepared by a literature-known method.

TABLE II

| Example No. | $R^2$ | Z | Salt-forming acid | m.p. °C. | Literature reference of the ketone component |
|---|---|---|---|---|---|
| 11. | H | 4-F-phenyl | HCl | 176–8 | J.A.C.S.63,974 (1941) |
| 12. | H | 4-Cl-phenyl | HCl | 178 | J.Chem.Soc.1947,231 |
| 13. | H | 4-Br-phenyl | HCl | 168 | Org.Synth.Coll.Vol.I.109 (1932) |
| 14. | H | 4-Br-phenyl | maleic acid | 142 | Org.Synth.Coll.Vol.I.109 (1932) |
| 15 | H | 3,4-diCl-phenyl | HCl | 188 | J.Chem.Soc.1927,1855 |
| 16. | H | 4-$NO_2$-phenyl | HCl | 197–8 | J.A.C.S.68,1386 (1946) |
| 17. | H | 4-(NH–CO–$CH_3$)-phenyl | HCl | 227–8 | Chem.Ber.42,3482 (1909) |
| 18. | H | 4-$OCH_3$-phenyl | HCl | 194–6 | J.Chem.Soc.1924,202 |
| 19. | H | 4-$OC_2H_5$-phenyl | HCl | 186–8 | J.A.C.S.76,(1954),5150 |
| 20. | H | 4-($OCH_2$-phenyl)-phenyl | HCl | 208–9 | J.Org.Chem.5,355 (1940) |
| 21. | H | 3-$OCH_3$-phenyl | HCl | 160–2 | J.Chem.Soc.1943,499 |

TABLE II-continued
| Example No. | R² | Z | Salt-forming acid | m.p. °C. | Literature reference of the ketone component |
|---|---|---|---|---|---|
| 22. | H | 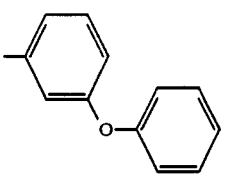 | HCl | 175 | J.A.C.S.58,1810 (1936) |
| 23. | H | 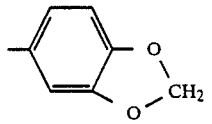 | HCl | 215–220 | Chem.Ber.36,3595 (1903) |
| 24. | H | 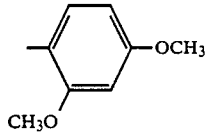 | HCl | 186–8 | Chem.Ber.24,2461 (1891) |
| 25. | H | 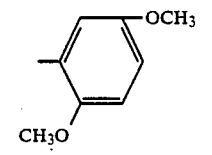 | HCl | 187–9 | Org.Synth.31.90 (1951) |
| 26. | H | 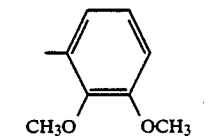 | HCl | 178–182 | J.A.C.S.52,3718 (1930) |
| 27. | H | 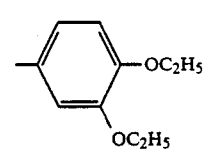 | HCl | 171–2 | Gazetta Chim.Ital.77,470 (1947) |
| 28. | H | 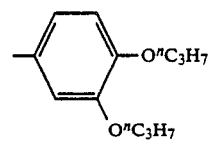 | HCl | 149–151 | |
| 29. | H | 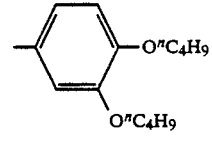 | HCl | 129–132 | J.Am.Pharm.Assoc.46,544 (1957) |
| 30. | H | 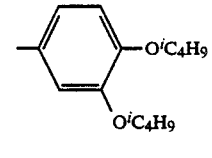 | HCl | 182–184 | |

TABLE II-continued

| Example No. | R² | Z | Salt-forming acid | m.p. °C. | Literature reference of the ketone component |
|---|---|---|---|---|---|
| 31. | H | 2,3,4-tri-OCH₃-phenyl | HCl | 201–3 | J.A.C.S.68, 1386 (1946) |
| 32. | H | 2,3,4-tri-OCH₃-phenyl (isomer) | HCl | 198–200 | Chem.Ber.44, 1551 (1911) |
| 33. | H | 4-CH₃-phenyl | HCl | 180–1 | J.A.C.S.46,1892 (1924) |
| 34. | H | 4-C₂H₅-phenyl | HCl | 188–9 | J.A.C.S.68,1107 (1946) |
| 35. | H | 4-iPr-phenyl | HCl | 181–3 | Chem.Ber.21,2225 (1983) |
| 36. | H | 4-(CH₂)₃–CH₃-phenyl | HCl | 124–7 | Chem.Ber.68,1831 (1935) |
| 37. | H | 4-(CH₂)₁₁–CH₃-phenyl | HCl | 103–112 | J.Org.Chem.20,520 (1953) |
| 38. | H | biphenyl | HCl | 202–5 | J.A.C.S.52,3718 (1930) |
| 39. | H | 3,4-di-CH₃-phenyl | HCl | 199–201 | J.A.C.S.64,423 (1942) |
| 40. | H | 2,4-di-CH₃-phenyl | HCl | 236–8 | J.A.C.S.59,804 (1937) |
| 41. | H | 4-OCH₃-naphthyl | HCl | 226–7 | Chem.Ber.47,3222 (1911) |

TABLE II-continued

| Example No. | R² | Z | Salt-forming acid | m.p. °C. | Literature reference of the ketone component |
|---|---|---|---|---|---|
| 42. | H | naphthalene with OC₂H₅ | | | |
| 43. | H | phenyl with OCH₃ and CH₃ | HCl | 181–3 | J.A.C.S.79 3585 (1 37) |
| 44. | H | phenyl with OCH₃ and Cl | HCl | 192–194 | J.Ind.Chem.Soc.36, 786 (1959) |
| 45. | H | phenyl with Cl and CH₃ | HCl | 228–9 | Chem.Ber.65,1297 (1932) |
| 46. | H | phenyl with OCH₃, Cl and HO | HCl | 197–9 | Indian J.Chem.2(7),298 |
| 47. | CH₃ | phenyl with F | maleic acid | 141–3 | J.Org.Chem.11,444 (1946) |
| 48. | CH₃ | phenyl with Cl | HCl | 200 | J.Org.Chem.11,444 (1946) |
| 49. | CH₃ | phenyl with Cl | maleic acid | 124–6 | J.Org.Chem.11,444 (1946) |
| 50. | CH₃ | phenyl with Br | HCl | 217–8 | J.Org.Chem.11,444 (1946) |
| 51. | CH₃ | phenyl with Br | HCl | 213 | J.Org.Chem.11,444 (1946) |
| 52. | CH₃ | phenyl with OCH₃ and OCH₃ | HCl | 140–2 | J.A.C.S.(63,531 (1941) |

TABLE II-continued

| Example No. | R² | Z | Salt-forming acid | m.p. °C. | Literature reference of the ketone component |
|---|---|---|---|---|---|
| 53. | ⁿC₁₀H₂₁ | phenyl | HCl | 98-101 | J.Org.Chem.8,139 (1943) |

The ketone components used in Examples 28 and 30 are prepared as follows:

3,4-Diisobutoxyacetophenone 33.35 g (0.15 mole) of 1,2-diisobutoxybenzene and then 14.72 g (0.187 mole) of acetyl chloride are added dropwise to a suspension containing 21.33 g (0.16 mole) of anhydrous aluminum chloride in 200 ml of dichloromethane, then the solution is heated in a water bath at 60° C. until the gas evolution ceases. The solution is then poured onto ice containing 20 ml of concentrated hydrochloric acid. After separation, the aqueous layer is extracted with dichloromethane, the combined organic phase is washed with 2N sodium hydroxide solution and then with water. The dichloromethane solution is dried over sodium sulfate, evaporated and the residue is distilled to give 12.10 g (30.5%) of the title ketone, b.p.: 148°-153° C./50 Pa (0.3 Hgmm). After recrystallization from hexane, the product melts at 72°-74° C.

3,4-Dipropoxyacetophenone 38.85 g (0.2 mole) of 1,2-dipropoxybenzene and then 19.63 g (0.25 mole) of acetyl chloride are added dropwise to a suspension containing 29.33 g (0.22 mole) of anhydrous aluminum chloride in 250 ml of dichloromethane under cooling by ice. The solution is boiled for 90 minutes, then cooled and poured onto ice containing 25 ml of concentrated hydrochloric acid. After separation, the aqueous layer is extracted with dichloromethane, the combined organic phase is washed with 2N sodium hydroxide solution and then with water. After drying, evaporation and distillation, 27.3 g (57.8%) of the title compound are obtained, b.p.: 150°-156° C./90 Pa (0.5 Hgmm). After recrystallization from hexane, the product melts at 51°-53° C.

EXAMPLES 54 TO 69

The compounds of the formula (XIII) listed in Table III, wherein R² means hydrogen, can be prepared in similar yields by using the process described in Example 1(a). In Table III, the meaning of Z and the melting point are given.

TABLE III

| Example No. | Z | m.p. °C. |
|---|---|---|
| 54. | 4-F-phenyl | 74 |
| 55. | 4-Cl-phenyl | 69 |
| 56. | 4-Br-phenyl | 94 |
| 57. | 4-NO₂-phenyl | 121 |
| 58. | 4-CH₃-phenyl | 94 |
| 59. | 4-C₄H₉-phenyl | 63 |
| 60. | 4-OCH₃-phenyl | 85 |
| 61. | 4-OC₂H₅-phenyl | 90 |
| 62. | 4-(O—CH₂—phenyl)-phenyl | 111 |
| 63. | 4-OEt-naphthyl | 79 |
| 64. | 3-OCH₃-phenyl | 60 |
| 65. | 4-NHCOCH₃-phenyl | 129 |

TABLE III-continued

| Example No. | Z | m.p. °C. |
|---|---|---|
| 66. | (phenyl with Cl, Cl substituents) | 62 |
| 67. | (phenyl with CH₃, CH₃ substituents) | 103 |
| 68. | (phenyl with O-CH₂-O methylenedioxy) | 71 |
| 69. | (phenyl with CH₃, Cl, OH substituents) | 143 |

EXAMPLE 70

2-(3,4-Dimethoxyphenyl)-6,6-diphenyl-3-methyl-3-azahexane hydrochloride

This compound can be prepared from 2-(3,4-dimethoxyphenyl)-6,6-diphenyl-3-azahexane with formic acid and formaldehyde in a 86% yield by using the process described in Example 8, m.p.: 180°–182° C.

EXAMPLE 71

6,6-di(4-Fluorophenyl)-2-(3,4-dimethoxyphenyl)-3-azahexane hydrochloride 5.68 g (0.02 mole) of 3,3-di(4-fluorophenyl)-propylamine hydrochloride (Andreu: Spanish patent specification No. 398,516; CA 83, 78816d) are mixed with 20 ml of 1N sodium hydroxide solution, then extracted with ether and the ethereal solution is evaporated. The thus-obtained base is reacted as described in Example (1a) with 3.6 g (0.02 mole) of 3,4-dimethoxyacetophenone to give the Schiff's base (m.p.: 94°–97° C.) which is then reduced according to Example (1b) to give the title compound in a yield of 56%, m.p.: 174°–176° C.

PREPARATION OF PHARMACEUTICAL COMPOSITION

EXAMPLE 72

(a) Tablets

|  | g |
|---|---|
| 2-(3,4-Dimethoxyphenyl)-6,6-diphenyl--3-azahexane hydrochloride | 100.0 |
| Corn starch | 130.0 |
| Calcium phosphate | 209.0 |
| Magnesium stearate | 1.0 |
|  | 440.0 |

The powdered mixture is compressed in a known manner to 1000 tablets each of which weighes 440 mg and contains 100 mg of the active ingredient.

(b) Depot dragées (sustained-release dragées)

|  | g |
|---|---|
| 2-(3,4-Dimethoxyphenyl)-6,6-diphenyl-3--azahexane hydrochloride | 150.0 |
| Carboxymethylcellulose | 300.0 |
| Stearic acid | 20.0 |
| Cellulose acetate phthalate | 30.0 |
|  | 500.0 |

The active ingredient, carboxymethylcellulose and stearic acid are thoroughly triturated with the solution of cellulose acetate phthalate in 200 ml of the solution of ethyl acetate in ethanol, compressed to dragées weighing 500 mg each and then coated in a known manner with 5% aqueous polyvinylpyrrolidone solution containing sugar. Each dragée contains 150 mg of the active ingredient.

(c) Injectable solution

|  |  |
|---|---|
| 2-(3,4-Dimethoxyphenyl)-6,6-diphenyl-3--azahexane hydrochloride | 50.0 g |
| Distilled water added up to | 1000.0 ml |

The active ingredient is dissolved in water in a known manner, then 1000 injections are prepared each of which contains 15 mg of the active ingredient in 1 ml of the solution.

We claim:

1. A compound of the formula (I)

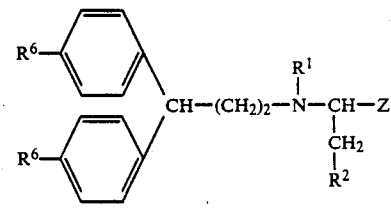

wherein
R¹ stands for hydrogen or a methyl group;
R² stands for hydrogen;
Z means a phenyl group substituted by R³, R⁴ and R⁵, wherein
R³ means hydrogen, or a nitro, $C_{1-12}$ alkyl, $C_{1-4}$ alkoxy, phenoxy or benzyloxy group;
R⁴ and R⁵ represent hydrogen, alkoxy, benzyloxy, acetamino or carboxy group; or
R⁴ and R⁵ together form a methylendioxy group; or
Z may stand for a 4-methoxynaphthyl or 4-ethoxynaphthyl group;
R⁶ is hydrogen,
with the proviso that R¹, R², R³, R⁴, R⁵ and R⁶ cannot simultaneously all stand for hydrogen,
or a physiologically acceptable acid addition salt thereof.

2. 2-(3,4-dimethoxy-phenyl)-6,6-diphenyl-3-azahexane or a pharmaceutically acceptable acid addition salt thereof as defined in claim 1.

3. A compound as claimed in claim 1 selected from the group consisting of:
2-(3,4-dimethoxyphenyl)-6,6-diphenyl-3-azahexane;
2-(4-methoxyphenyl)-6,6-diphenyl-3-azahexane;
2-(3-methoxyphenyl)-6,6-diphenyl-3-azahexane;
2-(3,4,5-trimethoxyphenyl)-6,6-diphenyl-3-azahexane; and
2-(4-methylphenyl)-6,6-diphenyl-3-azahexane; or a physiologically acceptable acid addition salt thereof.

4. A pharmaceutical composition for treating angina or arrhythmia, which comprises as active ingredient a therapeutically effective amount of a compound as defined in claim 1 or a physiologically acceptable acid addition salt thereof in admixture with inert, nontoxic carriers and/or additives commonly used in the pharmaceutical industry.

5. A compound selected from the group consisting of:
2-(3,4-dimethoxy-phenyl)-6,6-diphenyl-3-azahexane;
6,6-diphenyl-2-(diphenyl-4-yl)-3-azahexane;
2-(3,4-dimethylphenyl)-6,6-diphenyl-3-azahexane; and
2-(2,4-dimethylphenyl)-6,6-diphenyl-3-azahexane; or a physiologically acceptable acid addition salt thereof.

6. A pharmaceutical composition for treating angina or arrhythmia, which comprises as active ingredient, a therapeutically effective amount of a compound as defined in claim 5, or a physiologically acceptable acid addition salt thereof in admixture with inert, nontoxic, carriers and/or additives commonly used in the pharmaceutical industry.

* * * * *